(12) United States Patent
Nakamura et al.

(10) Patent No.: US 11,837,346 B2
(45) Date of Patent: Dec. 5, 2023

(54) DOCUMENT CREATION SUPPORT APPARATUS, METHOD, AND PROGRAM

(71) Applicant: FUJIFILM Corporation, Tokyo (JP)

(72) Inventors: Keigo Nakamura, Tokyo (JP); Yohei Momoki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/739,158

(22) Filed: May 8, 2022

(65) Prior Publication Data

US 2022/0262471 A1 Aug. 18, 2022

Related U.S. Application Data

(63) Continuation of application No. PCT/JP2020/044926, filed on Dec. 2, 2020.

(30) Foreign Application Priority Data

Dec. 3, 2019 (JP) ................................ 2019-218588

(51) Int. Cl.
*G06F 17/00* (2019.01)
*G16H 15/00* (2018.01)
*G06F 40/166* (2020.01)
*G06F 40/20* (2020.01)
*G06T 7/00* (2017.01)

(52) U.S. Cl.
CPC ........... *G16H 15/00* (2018.01); *G06F 40/166* (2020.01); *G06F 40/20* (2020.01); *G06T 7/0012* (2013.01)

(58) Field of Classification Search
CPC ........ G16H 15/00; G16H 30/40; G16H 50/20; G06F 40/166; G06F 40/20; G06F 40/30; G06F 40/56; G06F 40/169; G06T 7/0012; G06V 2201/03; A61B 5/055; A61B 6/00; A61B 6/03

See application file for complete search history.

(56) References Cited

U.S. PATENT DOCUMENTS 10,811,134 B2 * 10/2020 Bernard ................. A61B 6/503
10,825,178 B1 * 11/2020 Jeong ..................... G06N 20/00
10,891,352 B1 * 1/2021 Hane ...................... G06F 40/30
(Continued)

FOREIGN PATENT DOCUMENTS

CN 103324609 A * 9/2013 ......... G06F 17/2223
CN 109948166 A * 6/2019
(Continued)

OTHER PUBLICATIONS

"International Search Report (Form PCT/ISA/210) of PCT/JP2020/044926," dated Feb. 22, 2021, with English translation thereof, pp. 1-4.

(Continued)

*Primary Examiner* — Laurie A Ries
(74) *Attorney, Agent, or Firm* — JCIPRNET

(57) ABSTRACT

Provided is at least one processor, and the processor is configured to analyze an image to derive property information indicating a property of a structure of interest included in the image, generate a sentence related to the image based on the property information, analyze the sentence to specify a term representing the property related to the structure of interest included in the sentence, and collate the property information with the term.

15 Claims, 10 Drawing Sheets

(56) References Cited

U.S. PATENT DOCUMENTS

| | | | |
|---|---|---|---|
| 10,891,444 B2* | 1/2021 | Mori | G06V 10/25 |
| 10,910,100 B2* | 2/2021 | Harzig | G16H 50/20 |
| 11,062,800 B2* | 7/2021 | Lee | G06V 10/7788 |
| 11,322,256 B2* | 5/2022 | Sati | G16H 15/00 |
| 2007/0233465 A1* | 10/2007 | Sato | G06F 40/211 |
| | | | 704/10 |
| 2010/0189366 A1* | 7/2010 | Iizuka | G16H 15/00 |
| | | | 382/209 |
| 2011/0257963 A1* | 10/2011 | Zuev | G06F 40/30 |
| | | | 704/E11.001 |
| 2012/0060216 A1* | 3/2012 | Chaudhri | G06Q 10/10 |
| | | | 726/21 |
| 2012/0290328 A1* | 11/2012 | McCallie, Jr. | G06F 16/3331 |
| | | | 705/3 |
| 2014/0310607 A1* | 10/2014 | Abraham | G06F 16/2457 |
| | | | 715/738 |
| 2017/0286835 A1* | 10/2017 | Ho | G06F 40/247 |
| 2018/0011977 A1* | 1/2018 | Takeda | G16H 50/20 |
| 2018/0046614 A1* | 2/2018 | Ushio | G06N 3/044 |
| 2019/0034416 A1* | 1/2019 | Al Hasan | G06N 3/08 |
| 2019/0188848 A1* | 6/2019 | Madani | G16H 30/40 |
| 2019/0267132 A1* | 8/2019 | Fuchigami | G06T 11/60 |
| 2019/0279751 A1* | 9/2019 | Nakamura | G16H 30/40 |
| 2019/0295248 A1 | 9/2019 | Nakamura et al. | |
| 2020/0294654 A1* | 9/2020 | Harzig | G16H 15/00 |
| 2022/0083580 A1* | 3/2022 | Yamamoto | G06F 16/35 |
| 2022/0392060 A1* | 12/2022 | Themelis | G06F 18/24 |

FOREIGN PATENT DOCUMENTS

| | | |
|---|---|---|
| JP | 2009082443 | 4/2009 |
| JP | 2019149130 | 9/2019 |
| JP | 2019153250 | 9/2019 |
| JP | 2019169049 | 10/2019 |

OTHER PUBLICATIONS

"Written Opinion of the International Searching Authority (Form PCT/ISA/237)" of PCT/JP2020/044926, dated Feb. 22, 2021, with English translation thereof, pp. 1-7.

"Office Action of Japan Counterpart Application", dated Jul. 4, 2023, with English translation thereof, p. 1-p. 6.

* cited by examiner

DOCUMENT CREATION SUPPORT APPARATUS, METHOD, AND PROGRAM

CROSS REFERENCE TO RELATED APPLICATIONS

The present application is a Continuation of PCT International Application No. PCT/JP2020/044926, filed on Dec. 2, 2020, which claims priority to Japanese Patent Application No. 2019-218588, filed on Dec. 3, 2019. Each application above is hereby expressly incorporated by reference, in its entirety, into the present application.

BACKGROUND

Technical Field

The present disclosure relates to a document creation support apparatus, a method, and a program that support creation of documents such as medical documents.

Related Art

In recent years, advances in medical devices, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MM images, and the like, appropriate treatment is being performed based on the specified result.

In addition, image diagnosis is also made by analyzing a medical image by computer-aided diagnosis (CAD) using a learning model in which machine learning is performed by deep learning or the like, discriminating properties such as the shape, density, position, and size of structures of interest such as abnormal shadow candidates included in the medical images, and acquiring them as an analysis result. The analysis result acquired by CAD is associated with examination information such as a patient name, gender, age, and a modality that has acquired the medical image, and is saved in a database. The medical image and the analysis result are transmitted to a terminal of a radiologist who interprets the medical images. The radiologist interprets the medical image by referring to the transmitted medical image and analysis result and creates an interpretation report, in his or her own terminal.

Meanwhile, with the improvement of the performance of the CT apparatus and the MRI apparatus described above, the number of medical images to be interpreted is also increasing. However, since the number of radiologists has not kept up with the number of medical images, it is desired to reduce the burden of the image interpretation work of the radiologists. Therefore, various methods have been proposed to support the creation of medical documents such as interpretation reports. For example, JP2019-153250A proposes a method for generating a sentence to be described in an interpretation report based on keywords input by a radiologist and information indicating a property of a structure of interest (hereinafter referred to as property information) included in an analysis result of a medical image (see JP2019-153250A). In the methods described in JP2019-153250A, a sentence for medical care (hereinafter referred to as a medical sentence) is created by using a learning model in which machine learning is performed, such as a recurrent neural network trained to generate a sentence from characters representing the input property information. By automatically generating the medical sentence as in the method described in JP2019-153250A, it is possible to reduce a burden on a radiologist at the time of creating a medical document such as an interpretation report.

On the other hand, it is conceivable to generate a learning model that generates a medical sentence by using only the property information acquired by analyzing the medical image. However, depending on the content of teacher data used to train the learning model, or depending on the learning limits of the learning model, all property information acquired from the medical image may not be included in the generated medical sentence. In addition, property information other than the property information acquired from the medical image may be included in the generated medical sentence. In a case where such medical sentences are used as an interpretation report, the accuracy of the interpretation report will decrease.

SUMMARY OF THE INVENTION

The present disclosure has been made in view of the above circumstances, and an object of the present disclosure is to generate a sentence related to a structure of interest included in an image from the image with high accuracy, as in the case of generating a medical sentence from a medical image.

According to an aspect of the present disclosure, there is provided a document creation support apparatus comprising at least one processor, in which the processor is configured to analyze an image to derive property information indicating a property of a structure of interest included in the image, generate a sentence related to the image based on the property information, analyze the sentence to specify a term representing the property related to the structure of interest included in the sentence, and collate the property information with the term.

In the document creation support apparatus according to the aspect of the present disclosure, the processor may be further configured to display the sentence on a display.

In this case, the processor may be further configured to display a result of the collation on the display.

In the document creation support apparatus according to the aspect of the present disclosure, the processor may be further configured to display the result of the collation by highlighting a different point in a case where the term and the property information are different from each other in the sentence.

In the document creation support apparatus according to the aspect of the present disclosure, the processor may be further configured to regenerate the sentence in a case where the term and the property information are different from each other in the sentence.

In the document creation support apparatus according to the aspect of the present disclosure, the processor may be further configured to receive correction of the sentence.

In the document creation support apparatus according to the aspect of the present disclosure, the processor may be configured to generate a plurality of sentences related to the image based on the property information, analyze each of the plurality of sentences to specify a term representing the property related to the structure of interest included in each of the plurality of sentences, collate the property information with the term for each of the plurality of sentences, and select at least one sentence from the plurality of sentences based on a result of the collation.

In the document creation support apparatus according to the aspect of the present disclosure, the image may be a medical image, and the sentence may be a medical sentence related to the structure of interest included in the medical image.

According to another aspect of the present disclosure, there is provided a document creation support method comprising: analyzing an image to derive property information indicating a property of a structure of interest included in the image; generating a sentence related to the image based on the property information; analyzing the sentence to specify a term representing the property related to the structure of interest included in the sentence; and collating the property information with the term.

In addition, a program for causing a computer to execute the document creation support method according to the aspect of the present disclosure may be provided.

According to the aspects of the present disclosure, it is possible to generate a sentence related to a structure of interest included in an image from the image with high accuracy.

DETAILED DESCRIPTION

Figure 1:
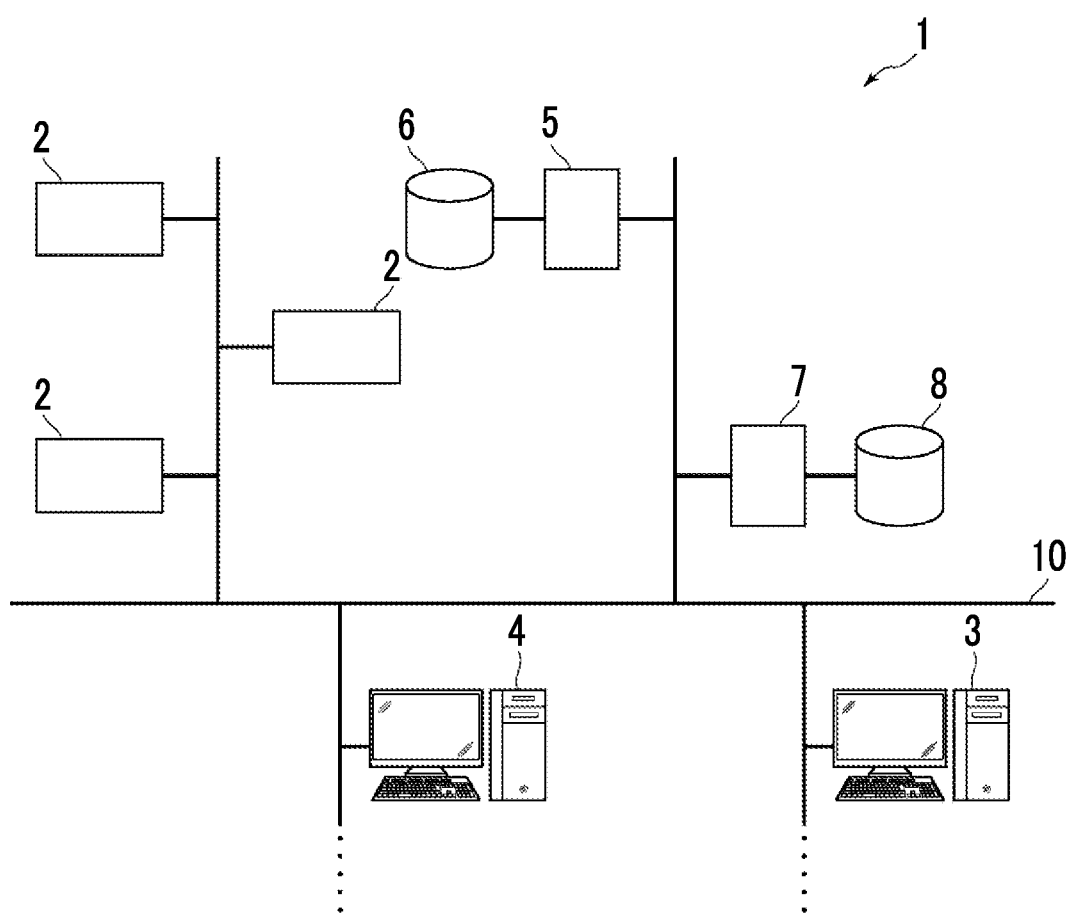
FIG. 1 is a diagram showing a schematic configuration of a medical information system to which a document creation support apparatus according to an embodiment of the present disclosure is applied.

Hereinafter, embodiments of the present disclosure will be described with reference to the drawings. FIG. 1 is a diagram showing a schematic configuration of a medical information system to which a document creation support apparatus according to an embodiment of the present disclosure is applied. A medical information system 1 shown in FIG. 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source. As shown in FIG. 1, the medical information system 1 is configured to include a plurality of modalities (imaging apparatuses) 2, a plurality of interpretation workstations (WS) 3 that are interpretation terminals, a medical department workstation (WS) 4, an image server 5, an image database 6, an interpretation report server 7, and an interpretation report database 8 that are communicably connected to each other through a wired or wireless network 10.

Each apparatus is a computer on which an application program for causing each apparatus to function as a component of the medical information system 1 is installed. The application program is stored in a storage apparatus of a server computer connected to the network 10 or in a network storage in a state in which it can be accessed from the outside, and is downloaded to and installed on the computer in response to a request. Alternatively, the optimization support program is recorded on a recording medium, such as a digital versatile disc (DVD) or a compact disc read only memory (CD-ROM), and distributed, and is installed on the computer from the recording medium.

The modality 2 is an apparatus that generates a medical image showing a diagnosis target part of the subject by imaging the diagnosis target part. Specifically, examples of the modality include a simple X-ray imaging apparatus, a CT apparatus, an MRI apparatus, a positron emission tomography (PET) apparatus, and the like. A medical image generated by the modality 2 is transmitted to the image server 5 and is saved therein.

The interpretation WS 3 encompasses the document creation support apparatus according to the present embodiment. The configuration of the interpretation WS 3 will be described later.

The medical department WS 4 is a computer used by a doctor in a medical department to observe an image in detail, view an interpretation report, create an electronic medical record, and the like, and is configured to include a processing apparatus, a display, and an input device such as a keyboard and a mouse. In the medical department WS 4, each process such as creating a medical record (electronic medical record) of a patient, requesting the image server 5 to view an image, displaying an image received from the image server 5, automatically detecting or highlighting a lesion-like portion in the image, requesting the interpretation report server 7 to view an interpretation report, and displaying the interpretation report received from the interpretation report server 7 is performed by executing a software program for each process.

The image server 5 is a general-purpose computer on which a software program that provides a function of a database management system (DBMS) is installed. The image server 5 comprises a storage in which the image database 6 is configured. This storage may be a hard disk apparatus connected to the image server 5 by a data bus, or may be a disk apparatus connected to a storage area network (SAN) or a network attached storage (NAS) connected to the network 10. In a case where the image server 5 receives a request to register a medical image from the modality 2, the image server 5 prepares the medical image in a format for a database and registers the medical image in the image database 6.

Image data of the medical image acquired by the modality 2 and accessory information are registered in the image database 6. The accessory information includes, for example, an image identification (ID) for identifying each medical image, a patient ID for identifying a subject, an examination ID for identifying an examination, a unique ID (UID: unique identification) allocated for each medical image, examination date and examination time at which a medical image is generated, the type of modality used in an examination for acquiring a medical image, patient information such as the name, age, and gender of a patient, an examination part (imaging part), imaging information (an imaging protocol, an imaging sequence, an imaging method, imaging conditions, the use of a contrast medium, and the like), and information such as a series number or a collection number when a plurality of medical images are acquired in one examination.

In addition, in a case where a viewing request from the interpretation WS 3 is received through the network 10, the image server 5 searches for a medical image registered in the image database 6 and transmits the searched for medical image to the interpretation WS 3 that is a request source.

The interpretation report server 7 incorporates a software program for providing a function of a database management system to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and confidence of the findings, is recorded.

In the present embodiment, it is assumed that the medical image is a three-dimensional CT image consisting of a plurality of tomographic images with the lung as a diagnosis target, and an interpretation report on an abnormal shadow included in the lung is created as a medical document by interpreting the CT image. The medical image is not limited to the CT image, and any medical image such as an MRI image and a simple two-dimensional image acquired by a simple X-ray imaging apparatus can be used.

The network 10 is a wired or wireless network that connects various apparatuses in a hospital to each other. In a case where the interpretation WS 3 is installed in another hospital or clinic, the network 10 may be configured to connect local area networks of respective hospitals through the Internet or a dedicated line.

Hereinafter, the interpretation WS 3 according to the present embodiment will be described in detail. The interpretation WS 3 is a computer used by a radiologist of a medical image to interpret the medical image and create an interpretation report, and is configured to include a processing apparatus, a display, and an input device such as a keyboard and a mouse. In the interpretation WS 3, each process such as requesting the image server 5 to view a medical image, various kinds of image processing on the medical image received from the image server 5, displaying the medical image, an analysis process on the medical image, highlighting the medical image based on the analysis result, creating the interpretation report based on the analysis result, supporting the creation of an interpretation report, requesting the interpretation report server 7 to register and view the interpretation report, and displaying the interpretation report received from the interpretation report server 7 is performed by executing a software program for each process. Note that, in these processes, processes other than those performed by the document creation support apparatus according to the present embodiment are performed by a well-known software program, and therefore the detailed description thereof will be omitted here. In addition, processes other than the processes performed by the document creation support apparatus according to the present embodiment may not be performed in the interpretation WS 3, and a computer that performs the processes may be separately connected to the network 10, and in response to a processing request from the interpretation WS 3, the requested process may be performed by the computer.

The document creation support apparatus according to the present embodiment is encompassed in the interpretation WS 3. Therefore, a document creation support program according to the present embodiment is installed on the interpretation WS 3. The document creation support program is stored in the storage apparatus of the server computer connected to the network or in the network storage in a state in which it can be accessed from the outside, and is downloaded to and installed on the interpretation WS 3 in response to a request. Alternatively, the medical document creation program is recorded on a recording medium such as a DVD or a CD-ROM, distributed, and is installed on the interpretation WS 3 from the recording medium.

Figure 2:
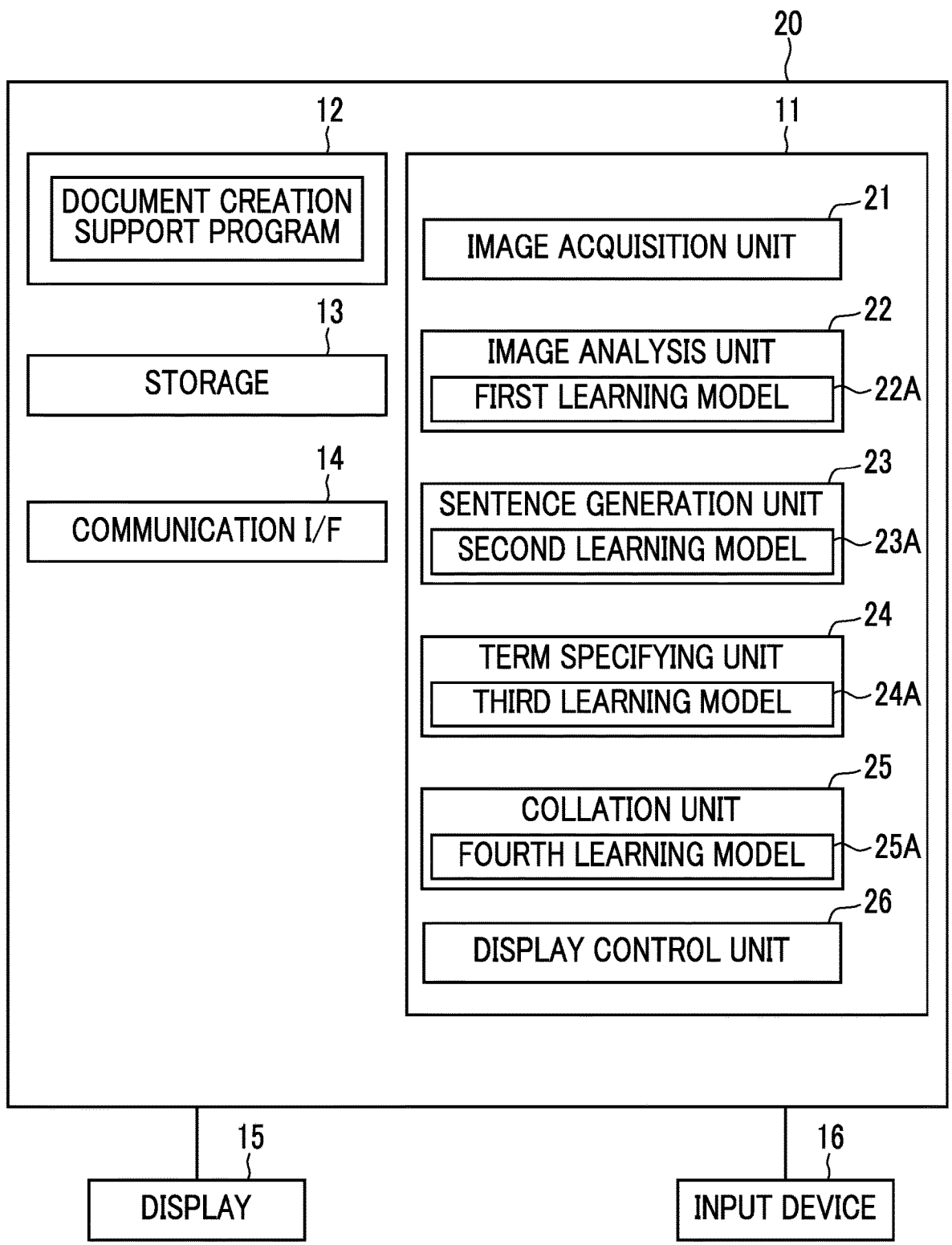
FIG. 2 is a diagram showing a schematic configuration of the document creation support apparatus according to the present embodiment.

FIG. 2 is a diagram showing a schematic configuration of the document creation support apparatus according to the present embodiment, which is realized by installing the document creation support program on the interpretation WS 3. As shown in FIG. 2, a document creation support apparatus 20 comprises a central processing unit (CPU) 11, a memory 12, a storage 13, and a communication interface (I/F) 14 as a standard computer configuration. Further, a display 15 such as a liquid crystal display and an input device 16 such as a keyboard and a mouse are connected to the document creation support apparatus 20. The CPU 11 corresponds to a processor.

The storage 13 consists of a storage device, such as a hard disk or a solid state drive (SSD). The storage 13 stores various kinds of information including medical images and information necessary for processing of the document creation support apparatus 20, which are acquired from the image server 5 through the network 10.

The communication I/F 14 is a network interface that controls transmission of various information between an external apparatus and the document creation support apparatus 20 via the network 10.

Further, the memory 12 stores a document creation support program. As processes to be executed by the CPU 11, the document creation support program defines an image acquisition process of acquiring a medical image, an image analysis process of deriving property information indicating a property of the structure of interest included in the medical image by analyzing the medical image, a sentence generation process of generating a medical sentence related to the medical image based on the property information, a term specifying process of specifying a term representing the property related to the structure of interest included in the medical sentence by analyzing the medical sentence, a collation process of collating the property information with the term, and a display control process of displaying the medical sentence and the collation result on the display 15.

Then, the CPU 11 executes the processes according to the document creation support program, so that the computer functions as an image acquisition unit 21, an image analysis unit 22, a sentence generation unit 23, a term specifying unit 24, a collation unit 25, and a display control unit 26.

The image acquisition unit 21 consists of an interface connected to the network 10, and acquires a medical image for creating an interpretation report from the image server 5 according to an instruction from the input device 16 by the radiologist who is an operator.

The image analysis unit 22 analyzes the medical image to derive property information indicating the property of the structure of interest such as an abnormal shadow candidate included in the medical image. For this purpose, the image analysis unit 22 has a first learning model 22A in which machine learning is performed so as to discriminate an abnormal shadow candidate in the medical image and discriminate the property of the discriminated abnormal shadow candidate. In the present embodiment, the first learning model 22A consists of a convolutional neural network (CNN) in which deep learning is performed using teacher data so as to discriminate whether or not each pixel (voxel) in the medical image represents an abnormal shadow candidate, and discriminate a property of a pixel in a case where the pixel represents an abnormal shadow candidate.

Figure 3:
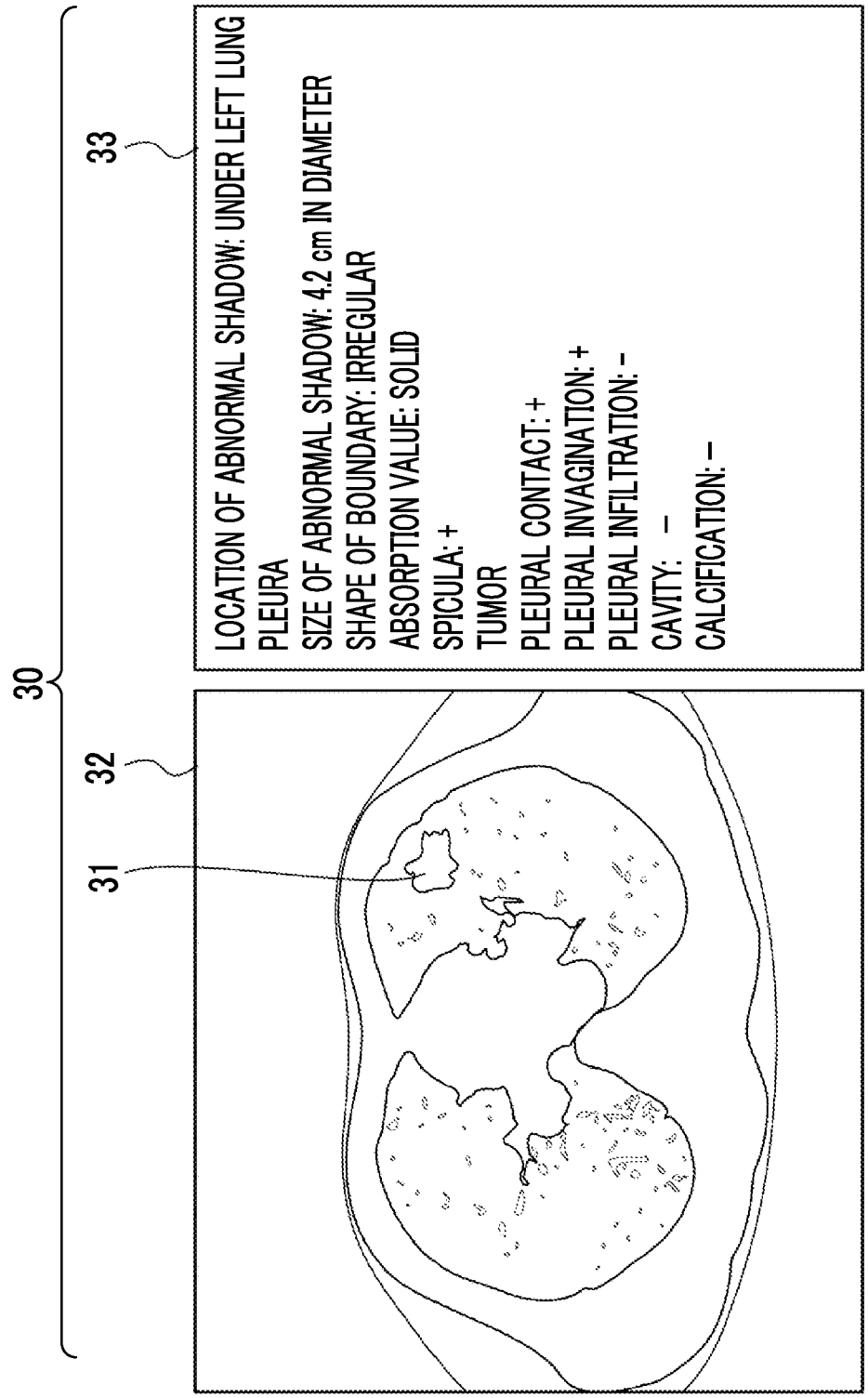
FIG. 3 is a diagram showing an example of teacher data for training a first learning model.

FIG. 3 is a diagram showing an example of teacher data for training a first learning model. As shown in FIG. 3, teacher data 30 includes a medical image 32 including an abnormal shadow 31 and property information 33 about the abnormal shadow. In the present embodiment, it is assumed that the abnormal shadow 31 is a lung nodule, and the property information 33 indicates a plurality of properties of the lung nodule. For example, as the property information 33, the location of the abnormal shadow, the size of the abnormal shadow, the shape of the boundary (clear and irregular), the type of absorption value (solid and frosted glass type), the presence or absence of spicula, whether it is a tumor or a nodule, the presence or absence of pleural contact, the presence or absence of the pleural invagination, the presence or absence of pleural infiltration, the presence or absence of a cavity, and the presence or absence of calcification are used. Regarding the abnormal shadow 31 included in the teacher data 30 shown in FIG. 3, the property information 33 indicates, as shown in FIG. 3, that the location of the abnormal shadow is under the left lung pleura, the size of the abnormal shadow is 4.2 cm in diameter, the shape of the boundary is irregular, the absorption value is a solid type, spicula is present, it is a tumor, pleural contact is present, pleural invagination is present, pleural infiltration is absent, a cavity is absent, and calcification is absent. In addition, in FIG. 3, + is given in the case of "present", and – is given in the case of "absent". The first learning model 22A is constructed by learning a neural network using a large amount of teacher data as shown in FIG. 3. For example, by using the teacher data 30 shown in FIG. 3, the first learning model 22A is trained to discriminate the abnormal shadow 31 included in the medical image 32 in a case where the medical image 32 shown in FIG. 3 is input, and output the property information 33 shown in FIG. 3 with regard to the abnormal shadow 31.

Further, as the first learning model 22A, any learning model such as, for example, a support vector machine (SVM) can be used in addition to the convolutional neural network.

Note that the learning model for detecting the abnormal shadow candidate from the medical image and the learning model for detecting the property information of the abnormal shadow candidate may be constructed separately.

Figure 4:
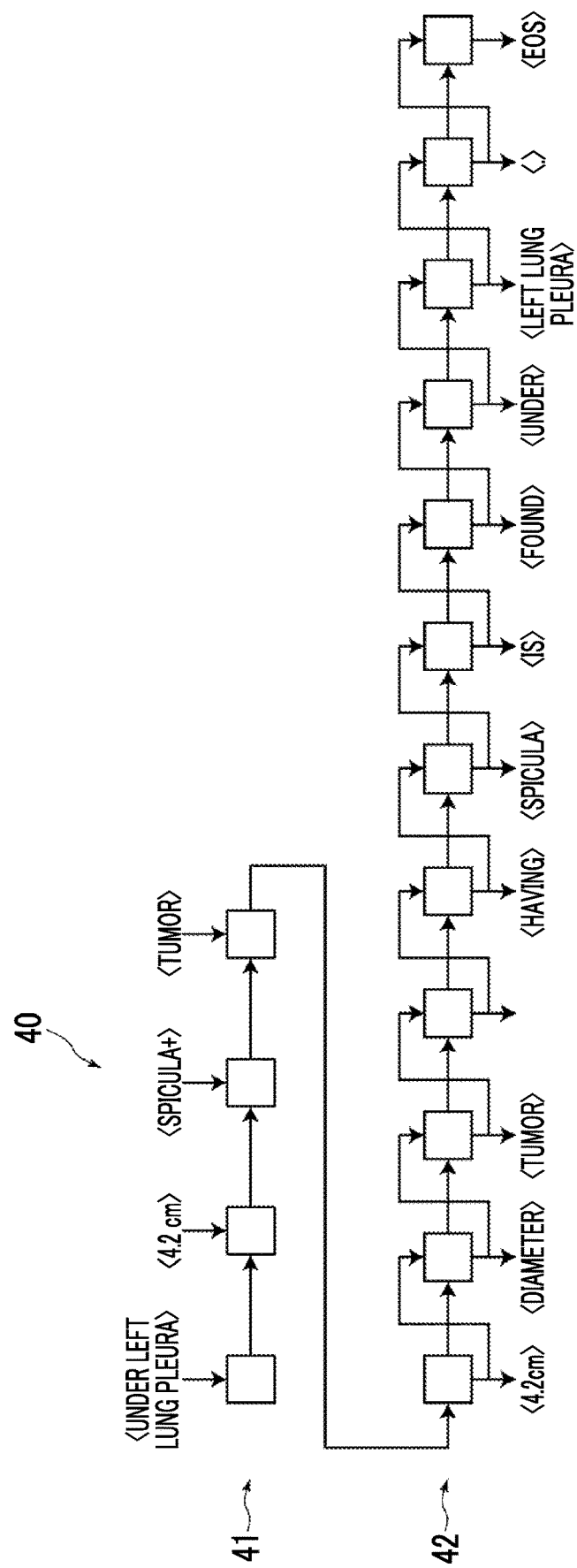
FIG. 4 is a diagram schematically showing a configuration of a recurrent neural network.

The sentence generation unit 23 generates a medical sentence by using the property information derived by the image analysis unit 22. The sentence generation unit 23 consists of a second learning model 23A that has been trained to generate a sentence from the input information. As the second learning model 23A, for example, a recurrent neural network can be used. FIG. 4 is a diagram schematically showing a configuration of a recurrent neural network. As shown in FIG. 4, the recurrent neural network 40 consists of an encoder 41 and a decoder 42. The property information derived by the image analysis unit 22 is input to the encoder 41. For example, property information indicating "under left lung pleura", "4.2 cm", "spicula +" and "tumor" is input to the encoder 41. The decoder 42 is trained to document character information, and generates a sentence from the input property information. Specifically, from the above-mentioned property information indicating "under left lung pleura", "4.2 cm", "spicula +" and "tumor", a medical sentence "A 4.2 cm diameter tumor having spicula is found under the left lung pleura." is generated. In FIG. 4, "EOS" indicates the end of the sentence (End Of Sentence).

In this way, in order to output the medical sentence by inputting the property information, the recurrent neural network 40 is constructed by learning the encoder 41 and the decoder 42 using a large amount of teacher data consisting of a combination of the property information and the medical sentence.

In the recurrent neural network 40, it is possible to designate terms that should not be used in the sentence and terms that should be used as the parameters for sentence generation. This parameter is determined based on a collation result by the collation unit 25 which will be described later.

The term specifying unit 24 specifies a term representing a property included in the medical sentence generated by the sentence generation unit 23. For this purpose, the term specifying unit 24 has a third learning model 24A in which machine learning is performed so as to specify a term representing a property included in a sentence. In the present embodiment, the third learning model 24A consists of a convolutional neural network in which deep learning is performed using the teacher data so as to discriminate the terms representing the properties included in the input sentence in a case where the sentence is input.

Figure 5:
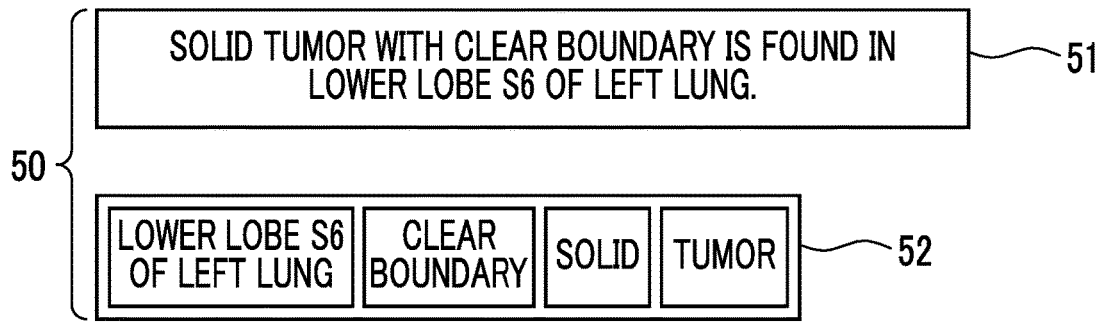
FIG. 5 is a diagram showing an example of teacher data for training a third learning model.

FIG. 5 is a diagram showing an example of teacher data for training the third learning model. As shown in FIG. 5, the teacher data 50 includes a medical sentence 51 and terms 52 representing the properties included in the medical sentence 51. The medical sentence 51 shown in FIG. 5 is "A solid tumor with a clear boundary is found in the lower lobe S6 of the left lung", and the terms 52 representing the properties are "lower lobe S6 of the left lung", "clear boundary", "solid", and "tumor" included in the medical sentence 51. The third learning model 24A is constructed by learning a neural network using a large amount of teacher data as shown in FIG. 5. For example, by using the teacher data 50 shown in FIG. 5, the third learning model 24A is trained such that the terms 52 shown in FIG. 5 are output in a case where the medical sentence 51 shown in FIG. 5 is input.

Further, as the third learning model 24A, for example, any learning model such as a support vector machine and a recurrent neural network can be used, in addition to the convolutional neural network.

The collation unit 25 collates the property information derived by the image analysis unit 22 with the term representing the property included in the medical sentence specified by the term specifying unit 24. For this purpose, the collation unit 25 has a fourth learning model 25A in which machine learning is performed so as to discriminate a difference between a term representing the property and property information in a case where the property information and the term representing the property are input, and to discriminate property information not included in the term representing the property and a term representing a property not included in the property information. In the present embodiment, the fourth learning model 25A consists of a convolutional neural network in which deep learning is performed using teacher data so as to discriminate a difference between a term representing the property and property information and to discriminate property information not included in the term representing the property and a term representing a property not included in the property information.

Figure 6:
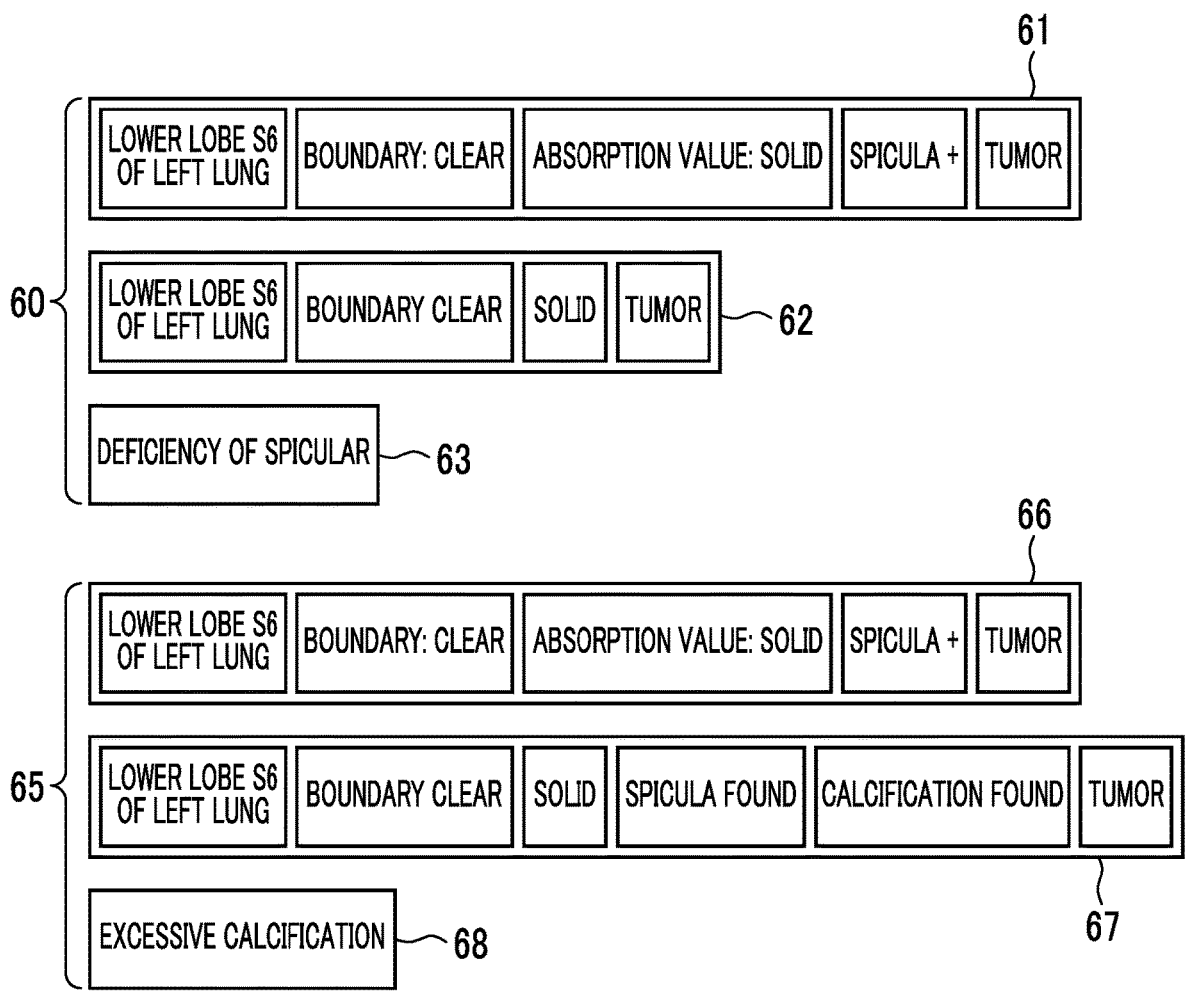
FIG. 6 is a diagram showing an example of teacher data for training a fourth learning model.

FIG. 6 is a diagram showing an example of teacher data for training a fourth learning model. FIG. 6 shows two types of teacher data 60 and 65. As shown in FIG. 6, the teacher data 60 includes property information 61, terms 62 representing the property, and excess/deficiency information 63 indicating the excess/deficiency of the property information. Further, teacher data 65 includes property information 66, terms 67 representing the property, and excess/deficiency information 68 indicating the excess/deficiency of the property information. With regard to the teacher data 60 shown in FIG. 6, the property information 61 is "lower lobe S6 of the left lung", "boundary: clear", "absorption value: solid", "spicula+" and "tumor". The terms 62 are "lower lobe S6 of the left lung", "boundary clear", "solid", and "tumor". The excess/deficiency information 63 is "deficiency of spicula".

With regard to the teacher data 65 shown in FIG. 6, similarly to the property information 61, the property information 66 is "lower lobe S6 of the left lung", "boundary; clear", "absorption value: solid", "spicula+" and "tumor". The terms 67 are "lower lobe S6 of the left lung", "boundary clear", "solid", "spicula found", "calcification found", and "tumor". The excess/deficiency information 68 is "excessive calcification".

The fourth learning model is constructed by learning a neural network using a large amount of teacher data as shown in FIG. 6. For example, by using the teacher data 60 shown in FIG. 6, the fourth learning model 25A is trained such that the excess/deficiency information 63 is output in a case where the property information 61 and the terms 62 representing the property shown in FIG. 6 are input. Further, learning is also performed so as to generate a parameter indicating that the term "spicula" is deficient as a parameter based on the collation result, based on the excess/deficiency information 63.

Further, by using the teacher data 65 shown in FIG. 6, the fourth learning model 25A is trained such that the excess/deficiency information 68 is output in a case where the property information 66 and the term 67 representing the property shown in FIG. 6 are input. Further, learning is also performed so as to generate a parameter indicating that the term "calcification" is excessive as a parameter based on the collation result, based on the excess/deficiency information 68.

As the fourth learning model 25A, for example, any machine learning model such as a support vector machine and a recurrent neural network can be used, in addition to the convolutional neural network.

Figure 7:
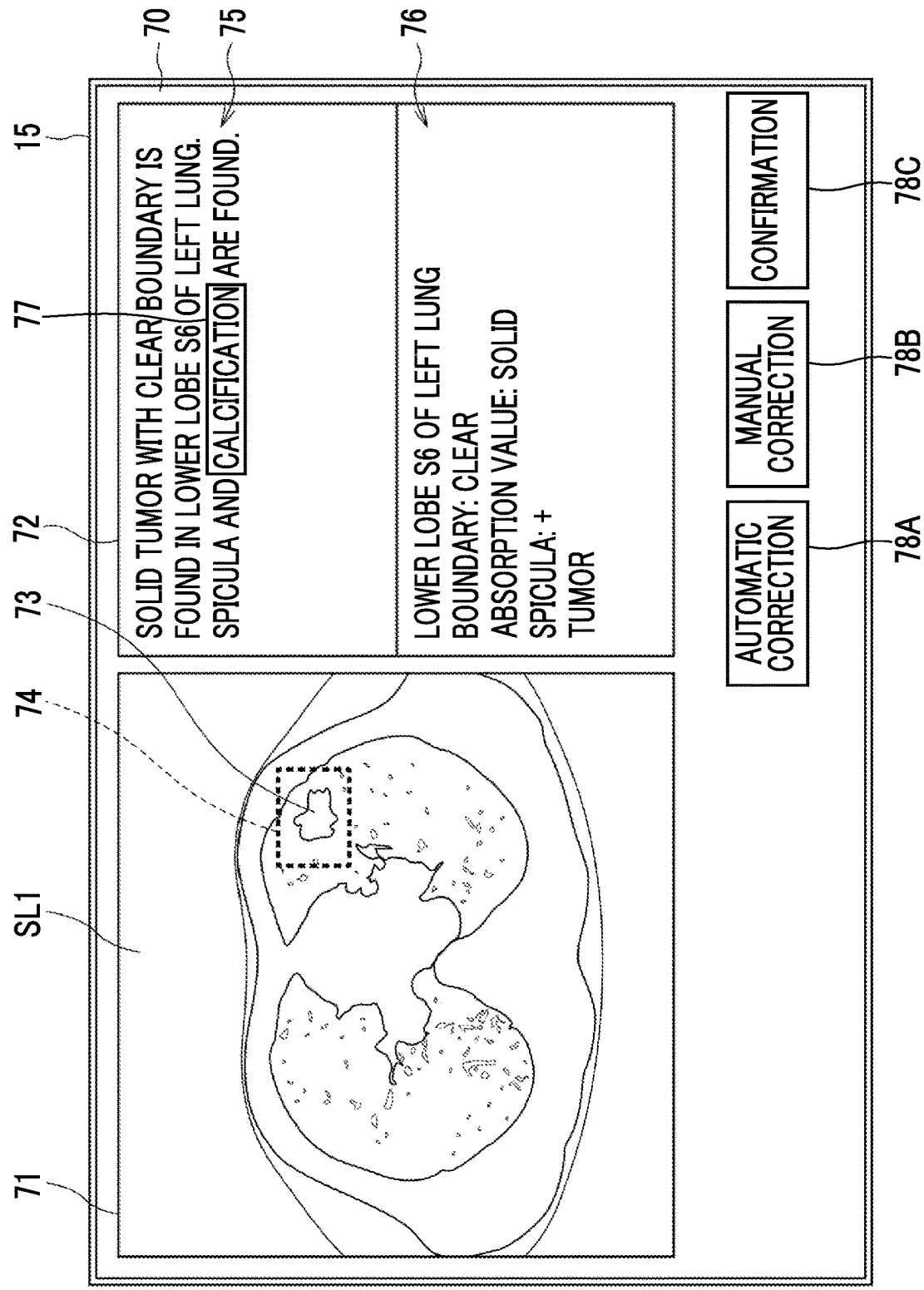
FIG. 7 is a diagram showing an example of a display screen of medical sentences and collation results.

The display control unit 26 displays the medical sentence generated by the sentence generation unit 23 and the collation result by the collation unit 25 on the display 15. FIG. 7 is a diagram showing an example of a display screen of medical sentences and collation results. As shown in FIG. 7, the display screen 70 includes an image display region 71 and a sentence display region 72. In the image display region 71, a slice image SL1 that is most likely to specify the abnormal shadow candidate detected by the image analysis unit 22 is displayed. The slice image SL1 includes an abnormal shadow candidate 73, and the abnormal shadow candidate 73 is surrounded by a rectangular region 74.

In the sentence display region 72, medical sentences 75 generated by the sentence generation unit 23 and property information 76 derived by the image analysis unit 22 are displayed. The property information 76 may not be displayed. The medical sentences 75 are "A solid tumor with a clear boundary is found in the lower lobe S6 of the left lung. Spicula and calcification are found.". The property information 76 is "lower lobe S6 of the left lung", "boundary: clear", "absorption value: solid", "spicula: +" and "tumor". Further, as a collation result, since "calcification" included in the medical sentence 75 is excessive, the term "calcification" included in the medical sentence 75 is given a solid line frame 77 indicating excess, and "calcification" is highlighted to display the collation result.

Below the sentence display region 72, an automatic correction button 78A, a manual correction button 78B, and a confirmation button 78C are displayed.

The radiologist interprets the slice image SL1 displayed in the image display region 71, and determines the suitability of the medical sentence 75 displayed in the sentence display region 72. Further, the radiologist can recognize that the term "calcification" included in the medical sentence 75 is excessive by the solid line frame 77 given to "calcification".

On the other hand, in a case where the radiologist desires to recreate the medical sentence 75, the automatic correction button 78A is selected using the input device 16. Thereby, the sentence generation unit 23 regenerates a medical sentence by using the property information derived by the image analysis unit 22. At this time, a parameter based on the collation result, that is, a parameter for avoiding the use of the term "calcification" is input to the second learning model 23A of the sentence generation unit 23. Thereby, the sentence generation unit 23 generates a medical sentence so as not to use the term "calcification", and as a result, it is possible to generate, for example, a medical sentence of "A solid tumor with a clear boundary is found in the lower lobe S6 of the left lung. Spicula is found.". In this case, a collation result shown in FIG. 9, which will be described later, will be displayed.

On the other hand, by selecting the manual correction button 78B, the radiologist can manually correct the medical sentence 75 displayed in the sentence display region 72 by input from the input device 16. Further, by selecting the confirmation button 78C, the medical sentence 75 displayed in the sentence display region 72 can be confirmed with its contents. Thereby, the medical sentence 75 is transcribed in an interpretation report, and the interpretation report to which the medical sentence 75 has been transcribed is transmitted to the interpretation report server 7 together with the slice image SL1 and stored therein.

Figure 8:
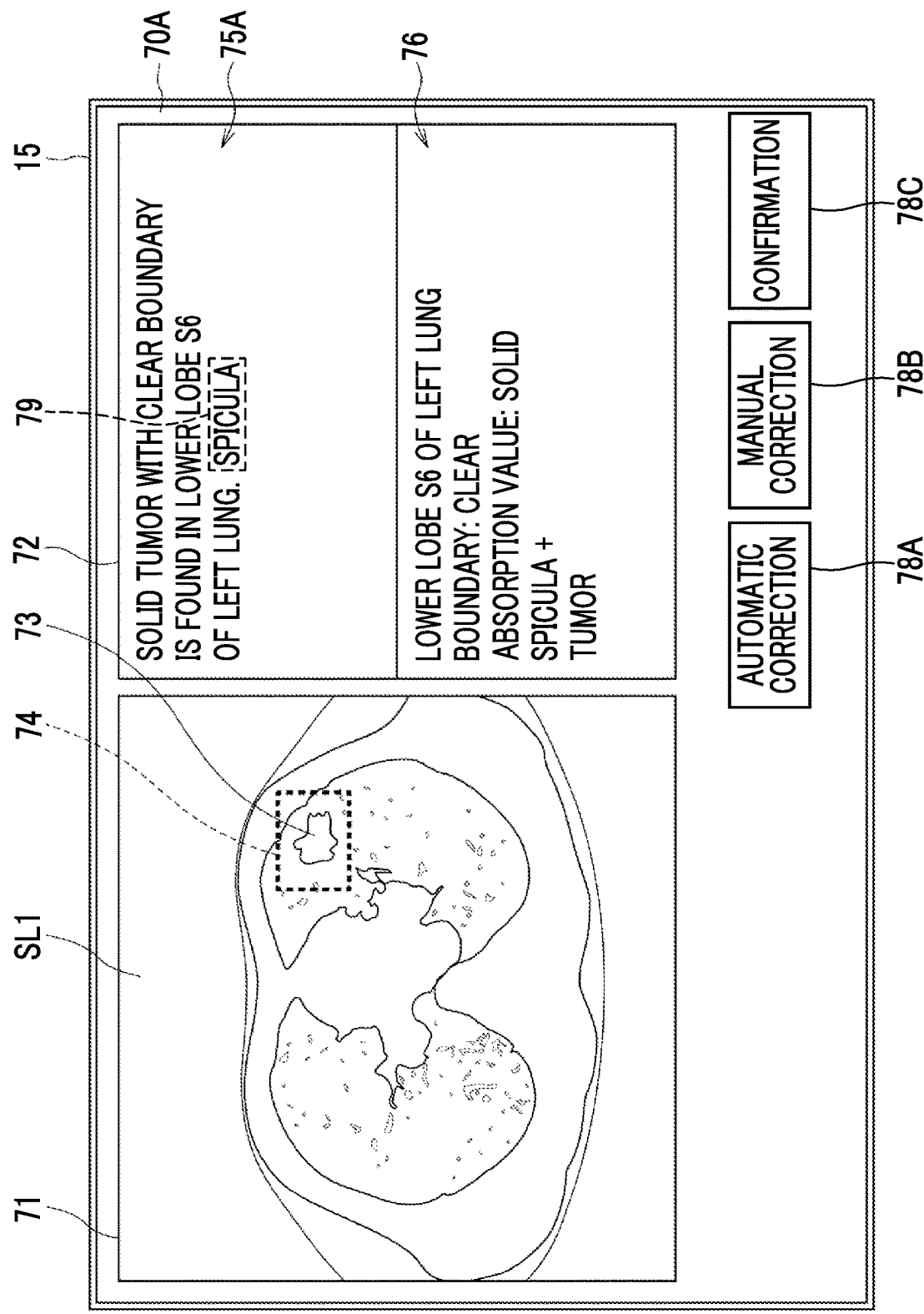
FIG. 8 is a diagram showing an example of a display screen of medical sentences and collation results.

FIG. 8 is a diagram showing another example of a display screen of medical sentences and collation results. In the display screen shown in FIG. 8, the same reference numerals are assigned to the same configurations as those in FIG. 7, and detailed description thereof will be omitted. In the sentence display region 72 of a display screen 70A shown in FIG. 8, a medical sentence 75A of "A solid tumor with a clear boundary is found in the lower lobe S6 of the left lung." is displayed.

Here, the property information 76 is "lower lobe S6 of the left lung", "boundary: clear", "absorption value: solid", "spicula: +" and "tumor". Further, in the medical sentence 75A, since the term "spicula" is deficient, the term "spicula" is displayed in the sentence display region 72, the term "spicula" included in the medical sentence 75A is given a broken-line frame 79 indicating deficiency, and the term "spicula" is highlighted to display the collation result.

Figure 9:
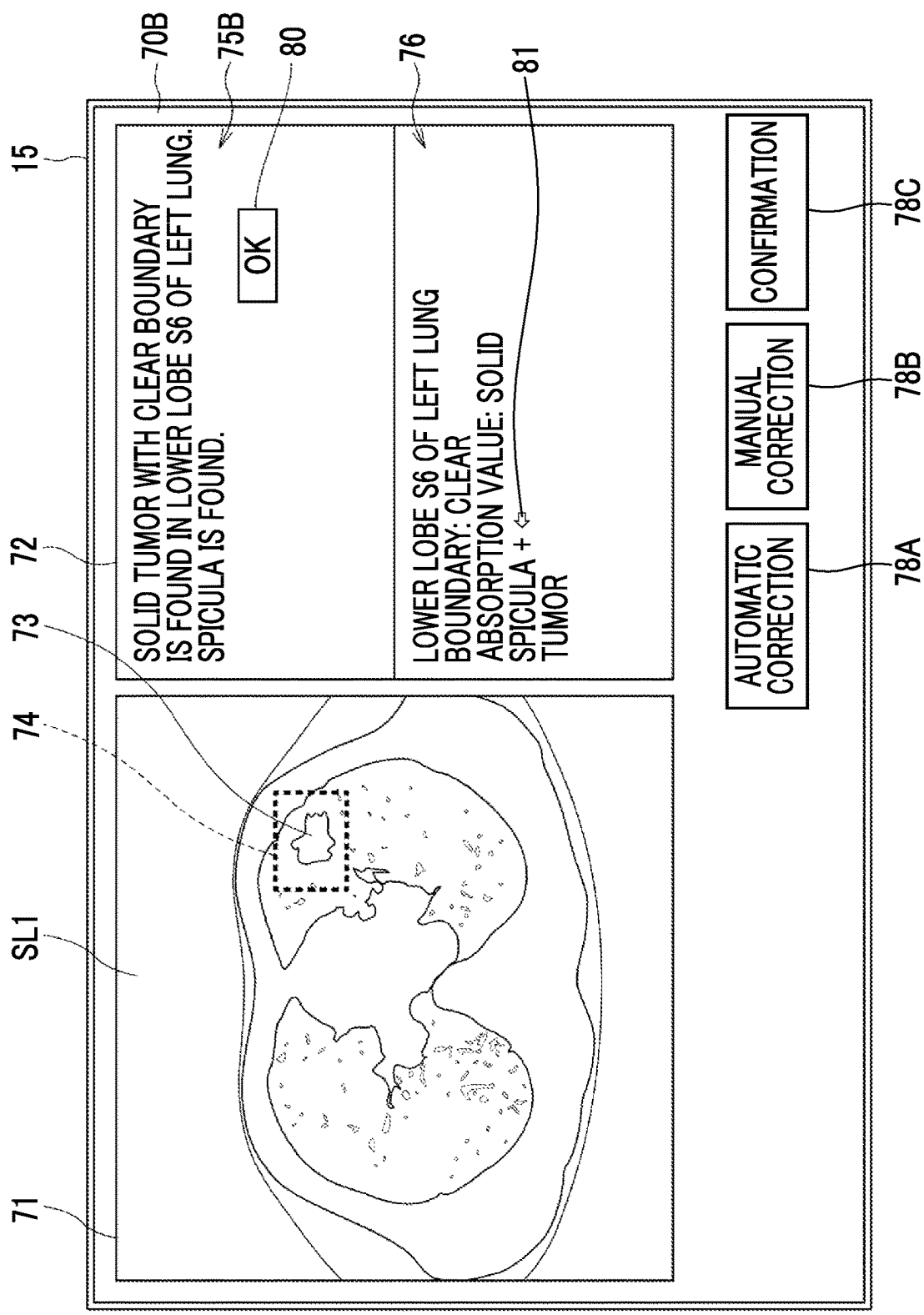
FIG. 9 is a diagram showing an example of a display screen of medical sentences and collation results.

With respect to the display screen 70A shown in FIG. 8, the radiologist interprets the abnormal shadow candidate 73 in the slice image SL1 displayed in the image display region 71, and determines the suitability of the medical sentence 75A displayed in the sentence display region 72. Further, the radiologist can recognize that the term "spicula" included in the medical sentence 75A is deficient by the broken-line frame 79 given to "spicula". In addition, instead of displaying the term "spicula" in the sentence display region 72 and adding the broken-line frame 79 indicating deficiency, or in addition to this, a mark such as an arrow or a frame may be added to indicate that the term "spicula" displayed in the property information 76 is deficient. FIG. 9 shows a state in which an arrow 81 indicating that the medical sentence 75A is insufficient is further added as a mark to the "spicula" displayed in the property information 76.

Then, in a case where the radiologist desires to recreate the medical sentence 75A, the automatic correction button 78A is selected using the input device 16. Thereby, the sentence generation unit 23 regenerates a medical sentence by using the property information derived by the image analysis unit 22. At this time, a parameter based on the collation result, that is, a parameter for using the term "spicula" is input to the learning model of the sentence generation unit 23. Thereby, the sentence generation unit 23 generates a medical sentence so as to use the term "spicula", and as a result, it is possible to generate, for example, a medical sentence of "A solid tumor with a clear boundary is found in the lower lobe S6 of the left lung. Spicula is found.". In this case, a collation result shown in FIG. 9, which will be described later, will be displayed. In this case, by adding the sentence "Spicula is found." to the medical sentence that has already been created, that is, "A solid tumor with a clear boundary is found in the lower lobe S6 of the left lung.", the medical sentence is generated. However, the entire medical sentence 75 may be regenerated.

In a case where the property information is displayed without excess or deficiency in the medical sentence displayed in the sentence display region 72, an OK mark 80 is displayed in the sentence display region 72, for example, as in the display screen 70B shown in FIG. 9. The radiologist can recognize that the property information derived from the medical image is used in "A solid tumor with a clear boundary is found in the lower lobe S6 of the left lung. Spicula is found.", which is the medical sentence 75B displayed in the sentence display region 72, without excess or deficiency by the OK mark 80.

Figure 10:
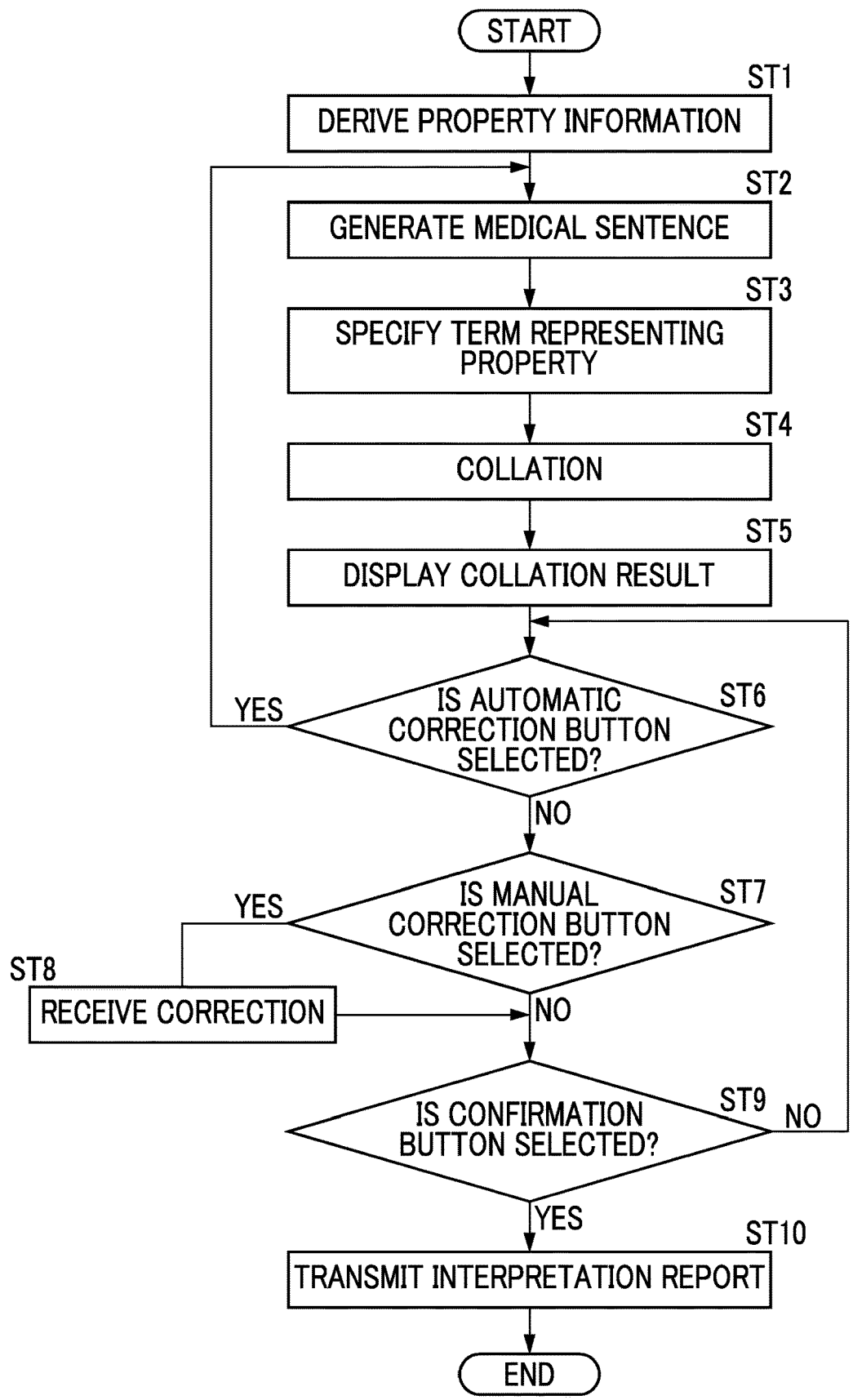
FIG. 10 is a flowchart showing a process performed in the present embodiment.

Next, a process performed in the present embodiment will be described. FIG. 10 is a flowchart showing a process performed in the present embodiment. It is assumed that the medical image to be interpreted is acquired from the image server 5 by the image acquisition unit 21 and is saved in the storage 13. The process is started in a case where an instruction to create an interpretation report is given by the radiologist, and the image analysis unit 22 analyzes the medical image to derive property information indicating the property of the structure of interest such as an abnormal shadow candidate included in the medical image (Step ST1). Next, the sentence generation unit 23 generates a medical sentence related to the medical image based on the property information (Step ST2). Subsequently, the term specifying unit 24 analyzes the medical sentence generated by the sentence generation unit 23 to specify the term representing the property related to the structure of interest included in the medical sentence (Step ST3). Further, the collation unit 25 collates the property information derived by the image analysis unit 22 with the term specified by the term specifying unit 24 (Step ST4). Then, the display control unit 26 displays the medical sentence generated by the sentence generation unit 23 and the collation result by the collation unit 25 on the display 15 (Step ST5).

Next, the display control unit 26 determines whether or not the automatic correction button 78A displayed on the display screen of the collation result is selected (Step ST6). In a case where step ST6 is affirmative, the process returns to Step ST2, and the processes of Steps ST2 to ST5 are repeated. Thereby, the sentence generation unit 23 regenerates the medical sentence according to the parameters based on the collation result. The term specifying unit 24 specifies terms in the regenerated medical sentence. The collation unit 25 collates the property information with the re-specified term. The display control unit 26 displays a display screen including the collation result again on the display 15.

In a case where Step ST6 is negative, the display control unit 26 determines whether or not the manual correction button 78B displayed on the display screen of the collation result is selected (Step ST7). In a case where Step ST7 is affirmative, the display control unit 26 receives the correction of the medical sentence displayed in the sentence display region 72 using the input device 16 (Step ST8).

In a case where Step ST7 is negative, and following Step ST8, the display control unit 26 determines whether or not the confirmation button 78C is selected (Step ST9). In a case where Step ST9 is negative, the process returns to Step ST6. In a case where Step ST9 is affirmative, the display control unit 26 transcribes the medical sentence to the interpretation report, and transmits the interpretation report to which the medical sentence is transcribed to the interpretation report server 7 together with the slice image SL1 (interpretation report transmission: Step ST10), and the process ends.

In this way, in the present embodiment, by analyzing the medical image, property information indicating the property of the structure of interest such as an abnormal shadow candidate included in the medical image is derived, and a medical sentence related to the medical image is generated based on the property information. Further, by analyzing the medical sentence, a term representing the property related to the structure of interest included in the medical sentence is specified, and the property information and the term are collated. Therefore, by referring to the collation result, it is possible to easily check whether the medical sentence is generated using all the property information and whether excessive property information is included in the sentence. Thereby, by referring to the collation result, the medical sentence can be corrected or the medical sentence can be regenerated, and the accuracy of the generated medical sentence can be improved. Therefore, according to the present embodiment, it is possible to generate a medical sentence related to a structure of interest included in a medical image from the medical image with high accuracy.

Figure 11:
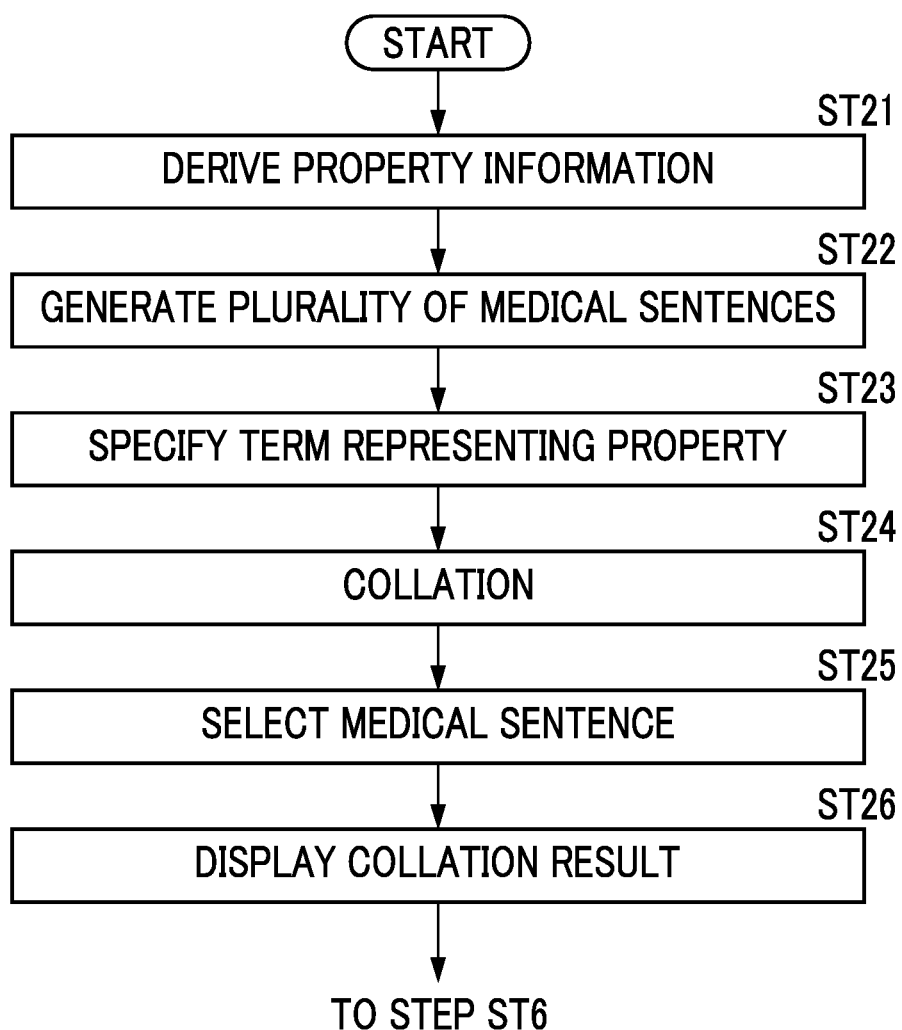
FIG. 11 is a flowchart showing a process performed in another embodiment.

Next, another embodiment of the present disclosure will be described. Since the configuration of a document creation support apparatus according to another embodiment is the same as that of the document creation support apparatus 20 shown in FIG. 2 and only the processing to be performed is different, detailed description of the apparatus will be omitted here. The document creation support apparatus according to another embodiment is different from the above embodiment in that the sentence generation unit 23 generates a plurality of medical sentences based on the property information. FIG. 11 is a flowchart showing a process performed in another embodiment. In another embodiment, the processes up to Step ST5 shown in FIG. 10 are different from the above embodiment. Therefore, in FIG. 11, only the differences from the flowchart shown in FIG. 10 will be described.

The process is started in a case where an instruction to create an interpretation report is given by the radiologist, and the image analysis unit 22 analyzes the medical image to derive property information indicating the property of the structure of interest such as an abnormal shadow candidate included in the medical image (Step ST21). Next, the sentence generation unit 23 generates a plurality of medical sentences related to the medical image based on the property information (Step ST22).

The plurality of medical sentences can be generated, for example, by applying a beam search method described in "https://geekyisawesome.blogspot.com/2016/10/using-beam-search-to-generate-most.html" to the recurrent neural network 40 constituting the second learning model 23A. The beam search method is a method of searching for a word that appears next to a certain word in consideration of the probability of appearance of the word that appears next to a certain word. In another embodiment, the sentence generation unit 23 applies the beam search method to the recurrent neural network 40 to generate a plurality of (for example, five) medical sentences having a high probability of appearance of the word.

Subsequently, the term specifying unit 24 analyzes each of the plurality of medical sentences generated by the sentence generation unit 23 to specify the term representing the property related to the structure of interest included in each of the plurality of medical sentences as the content (Step ST23). Further, the collation unit 25 collates the property information derived by the image analysis unit 22 with the term specified by the term specifying unit 24 for each of the plurality of medical sentences (Step ST24), and selects one medical sentence from the plurality of medical sentences based on the result of the collation (Step ST25). At this time, the collation unit 25 may select the medical sentence in which the property information and the term match best. The collation unit 25 may select a medical sentence in which the order in which the property information is described in the sentence most matches best the order of the property information derived by the image analysis unit 22. Then, the display control unit 26 displays the selected medical sentence and the collation result by the collation unit 25 on the display 15 (Step ST26), and proceeds to the process of Step ST6 shown in FIG. 10.

In this way, in another embodiment, a plurality of medical sentences are generated, and the medical sentence having the best match between the property information and the term is selected from the plurality of medical sentences. Therefore, it is possible to present a medical sentence in which there is little difference between the property information and the included term to the radiologist together with the collation result. Therefore, the frequency of correcting the medical sentence and regenerating the medical sentence can be reduced, and as a result, the burden on the radiologist who creates the interpretation report can be reduced.

Although one medical sentence is selected from a plurality of medical sentences in the above other embodiment, two or more medical sentences may be selected. In this case, among a plurality of medical sentences, a high-ranking predetermined number of medical sentences having a high degree of matching between the property information and the term may be selected. Further, in a case where a plurality of medical sentences are selected, it is preferable that the plurality of medical sentences and the collation results for each of the plurality of medical sentences are displayed on the display 15 so that the radiologist can select the desired medical sentences.

Further, in each of the above embodiments, the solid line frame 77 is added to the "excess" term in the medical sentence 75 displayed in the sentence display region 72 of the display screen 70 shown in FIG. 7, the "deficiency" term in the medical sentence 75A displayed in the sentence display region 72 of the display screen 70A shown in FIG. 8 is displayed, and the broken-line frame 79 is added to the "deficiency" term. However, the present disclosure is not limited thereto. In a case where it is possible to distinguish and highlight the "excess" term and the "deficiency" term, it is possible to use any display aspect such as changing the color of the characters, adding a different types of broken lines, or changing the color to be highlighted. Further, the excess or deficiency of terms may be notified by voice.

Further, in each of the above embodiments, the collation unit 25 comprises the fourth learning model 25A, but the present disclosure is not limited thereto. As long as it can be determined whether or not the property information derived by the image analysis unit 22 and the term representing the property included in the medical sentence specified by the term specifying unit 24 match, any method other than the learning model can be applied.

Further, in each of the above embodiments, the medical sentence 75 is recreated based on the selection of the automatic correction button 78A, but the present disclosure is not limited thereto. As a result of collation by the collation unit 25, in a case where the property information derived by the image analysis unit 22 and the property included in the medical sentence specified by the term specifying unit 24 do not match, the sentence generation unit 23 may recreate the medical sentence 75 based on the result of the collation without waiting for the selection of the automatic correction button 78A.

Further, in each of the above embodiments, the display control unit 26 displays both the medical sentence generated by the sentence generation unit 23 and the collation result by the collation unit 25, but the present disclosure is not limited thereto. Only medical sentence may be displayed on the display screen 70 displayed on the display 15. In this case, for example, by giving an instruction to display the collation result from the input device 16, the "excess" term or the "deficiency" term in the medical document may be highlighted or the OK mark 80 may be displayed as in each of the above embodiments.

Further, in each of the above embodiments, the creation support process for the medical document such as the interpretation report is performed by generating the medical sentence using the medical image with the lung as the diagnosis target, but the diagnosis target is not limited to the lung. In addition to the lung, any part of a human body such as a heart, liver, brain, and limbs can be diagnosed. In this case, for each learning model of the image analysis unit 22, the sentence generation unit 23, and the term specifying unit 24, learning models that perform the analysis process, the sentence generation process, and the term specifying process according to the diagnosis target are prepared, a learning model that performs the analysis process, the sentence generation process, and the term specifying process according to the diagnosis target is selected, and a process of generating a medical sentence is executed.

In addition, in each of the above embodiments, although the technique of the present disclosure is applied to the case of creating an interpretation report as a medical document, the technique of the present disclosure can also be applied to a case of creating medical documents other than the interpretation report, such as an electronic medical record and a diagnosis report.

Further, in each of the above embodiments, the medical sentence is generated using the medical image, but the present disclosure is not limited thereto. Of course, the technique of the present disclosure can also be applied even in a case where a sentence targeting any image other than a medical image is generated.

Further, in each of the above embodiments, for example, as hardware structures of processing units that execute various kinds of processing, such as the image acquisition unit 21, the image analysis unit 22, the sentence generation unit 23, the term specifying unit 24, the collation unit 25, and the display control unit 26, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by using one or more of the above-described various processors as hardware structures.

Furthermore, as the hardware structure of the various processors, more specifically, an electrical circuit (circuitry) in which circuit elements such as semiconductor elements are combined can be used.

What is claimed is:

1. A document creation support apparatus comprising at least one processor,
   wherein the processor is configured to
   analyze an image to derive property information describing a property of a structure of interest included in the image,
   input the property information into a learning model to generate a sentence related to the image, wherein the learning model is trained by a combination of a plurality of pieces of training property information derived from a plurality of training images and a plurality of medical sentences generated from the plurality of pieces of training property information,
   analyze the sentence to specify a term representing the property related to the structure of interest included in the sentence,
   collate the property information with the term, and
   in response to the property information not being collated with the term, generate a parameter to indicate that the term is either excess information or deficiency information with respect to the property information and regenerate another sentence by using the learning model according to the parameter.

2. The document creation support apparatus according to claim 1, wherein the processor is further configured to display the sentence on a display.

3. The document creation support apparatus according to claim 2, wherein the processor is further configured to display a result of the collation on the display.

4. The document creation support apparatus according to claim 3, wherein the processor is further configured to display the result of the collation by highlighting a different point in a case where the term and the property information are different from each other in the sentence.

5. The document creation support apparatus according to claim 1, wherein the processor is further configured to regenerate the sentence in a case where the term and the property information are different from each other in the sentence.

6. The document creation support apparatus according to claim 1, wherein the processor is further configured to receive correction of the sentence.

7. The document creation support apparatus according to claim 1, wherein the processor is configured to
   generate a plurality of sentences related to the image based on the property information,
   analyze each of the plurality of sentences to specify a term representing the property related to the structure of interest included in each of the plurality of sentences,
   collate the property information with the term for each of the plurality of sentences, and
   select at least one sentence from the plurality of sentences based on a result of the collation.

8. The document creation support apparatus according to claim 1, wherein the image is a medical image, and the sentence is a medical sentence related to the structure of interest included in the medical image.

9. The document creation support apparatus according to claim 1, wherein the machine learning model is a recurrent neural network.

10. The document creation support apparatus according to claim 1, wherein after a result of the collation is generated, the processor is further configured to
    determine whether an automatic correction option is selected,
    in response to the automatic correction option being selected, regenerate another sentence related to the image,
    in response to the automatic correction option not being selected, determine whether a manual correction option is selected, and
    in response to the manual correction option being selected, receive a manual correction to the sentence.

11. The document creation support apparatus according to claim 1,
    wherein the machine learning model is a recurrent neural network constructed by learning an encoder and a decoder using the combination of the plurality of pieces of training property information and the plurality of medical sentences.

12. The document creation support apparatus according to claim 1, wherein the plurality of pieces of training property information are derived from the training images through image analysis, and wherein each of the plurality of pieces of training property information is at least one word that describes a property of a structure of interest included in the corresponding training image.

13. The document creation support apparatus according to claim 1, wherein the processor is further configured to:

in response to the term being excessive information with respect to the property information, regenerate another sentence by using the learning model such that the term is designated to be not included in the another sentence, and in response to the term being deficiency information with respect to the property information, regenerate another sentence by using the learning model such that the term is designated to be included in the another sentence.

14. A document creation support method comprising:

analyzing an image to derive property information describing a property of a structure of interest included in the image;

inputting the property information into a learning model to generate a sentence related to the image, wherein the learning model is trained by a combination of a plurality of pieces of training property information derived from a plurality of training images and a plurality of medical sentences generated from the plurality of pieces of training property information;

analyzing the sentence to specify a term representing the property related to the structure of interest included in the sentence;

collating the property information with the term, and in response to the property information not being collated with the term, generating a parameter to indicate that the term is either excess information or deficiency information with respect to the property information and regenerating another sentence by using the learning model according to the parameter.

15. A non-transitory computer-readable storage medium that stores a document creation support program causing a computer to execute a procedure comprising:

analyzing an image to derive property information describing a property of a structure of interest included in the image;

inputting the property information into a learning model to generate a sentence related to the image, wherein the learning model is trained by a combination of a plurality of pieces of training property information derived from a plurality of training images and a plurality of medical sentences generated from the plurality of pieces of training property information;

analyzing the sentence to specify a term representing a property related to the structure of interest included in the sentence;

collating the property information with the term; and in response to the property information not being collated with the term, generating a parameter to indicate that the term is either excess information or deficiency information with respect to the property information and regenerating another sentence by using the learning model according to the parameter.

* * * * *